US009476085B2

(12) United States Patent
Taylor et al.

(10) Patent No.: US 9,476,085 B2
(45) Date of Patent: *Oct. 25, 2016

(54) BACTERIAL IDENTIFICATION (71) Applicants: ARIZONA BOARD OF REGENTS ON BEHALF OF ARIZONA STATE UNIVERSITY, Scottsdale, AZ (US); LaKeta Kemp, Tempe, AZ (US)

(72) Inventors: Thomas Taylor, Tempe, AZ (US); Mark Hayes, Gilbert, AZ (US); LaKeta Kemp, Tempe, AZ (US); Paul Jones, Mesa, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/874,021

(22) Filed: Oct. 2, 2015

(65) Prior Publication Data

US 2016/0024550 A1 Jan. 28, 2016

Related U.S. Application Data

(62) Division of application No. 13/797,181, filed on Mar. 12, 2013, now Pat. No. 9,185,356.

(60) Provisional application No. 61/638,316, filed on Apr. 25, 2012.

(51) Int. Cl.
| | | |
|---|---|---|
| *C12Q 1/10* | (2006.01) | |
| *H04N 7/18* | (2006.01) | |
| *C12M 1/00* | (2006.01) | |
| *C12Q 1/24* | (2006.01) | |
| *B03C 5/00* | (2006.01) | |
| *B03C 5/02* | (2006.01) | |
| *G01N 27/447* | (2006.01) | |
| *B01D 57/02* | (2006.01) | |

(52) U.S. Cl.
CPC ............... *C12Q 1/10* (2013.01); *B03C 5/005* (2013.01); *B03C 5/026* (2013.01); *C12M 47/04* (2013.01); *C12Q 1/24* (2013.01); *G01N 27/44773* (2013.01); *G01N 27/44791* (2013.01); *H04N 7/18* (2013.01); *B01D 57/02* (2013.01); *B03C 2201/26* (2013.01)

(58) Field of Classification Search
CPC ....................................................... H04N 7/18
See application file for complete search history.

(56) References Cited

U.S. PATENT DOCUMENTS

| | | | |
|---|---|---|---|
| 9,185,356 B2 | 11/2015 | Taylor et al. | |
| 2011/0053793 A1* | 3/2011 | Monasterio | G01N 33/56944 506/9 |
| 2012/0021453 A1* | 1/2012 | Patra | G01N 15/147 435/34 |

OTHER PUBLICATIONS

Adelson, et al., "Pyramid methods in image processing", RCA Engineer,, vol. 29, No. 6, pp. 33-34 (Nov./Dec. 1984).

(Continued)

*Primary Examiner* — Dave Czekaj
*Assistant Examiner* — Nam Pham
(74) *Attorney, Agent, or Firm* — Viksnins Harris & Padys PLLP (57) ABSTRACT

The present invention provides for separation of bacterial species and serotypes using electrophoretic methods.

8 Claims, 5 Drawing Sheets

(56) References Cited

OTHER PUBLICATIONS

Armstrong, et al., "Mechanistic aspects in the generation of apparent ultrahigh efficiencies for colloidal (microbial) electrokinetic separations", Analytical Chemistry, 2002. 74(21): p. 5523-5530.

Armstrong, et al., "Rapid identification of the bacterial pathogens responsible for urinary tract infections using direct injection CE", Analytical Chemistry, 2000. 72(18): p. 4474-4476.

Armstrong, et al., "Separating microbes in the manner of molecules. 1. Capillary electrokinetic approaches", Analytical Chemistry, 1999. 71(24): p. 5465-5469.

Borges, et al., "Building Multidimensional Biomarker Views of Type 2 Diabetes Based on Protein Microheterogeneity", Clinical Chemistry, 2011. 57(5): p. 719-728.

Buszewski, et al., "Determination of pathogenic bacteria by CZE with surface-modified capillaries", Electrophoresis, 2008. 29(20): p. 4177-4184.

Chen, et al., "Biocompatible polymer materials: Role of protein-surface interactions", Progress in Polymer Science, 2008. 33(11): p. 1059-1087.

Chen, et al., "Insulator-based Dielectrophoretic Separations of Small Particles in Sawtooth Channel", Electrophoresis, 2009. 30: p. 1441-1448.

Cole, et al., "Visual Object Recognition using Template Matching", Proc. of Australian Conf. Robotics and Automation 2004.

Crowley, et al., "Analysis of human blood serum using the off-line coupling of capillary isoelectric focusing to matrix-assisted laser desorption/ionization time of flight mass spectrometry", Proteomics, 2005. 5(14): p. 3798-3804.

Garcia, et al., "Magnetic movement of biological fluid droplets", Journal of Magnetism and Magnetic Materials, 2007. 311(1): p. 238-243.

Gu, et al., "Preparation and evaluation of poly (polyethylene glycol methyl ether acrylate-co-polyethylene glycol diacrylate) monolith for protein analysis", Journal of Chromatography A, 2005. 1079(1-2): p. 382-391.

Hartley, et al., "Examination of Theoretical Models in External Voltage Control of Capillary Electrophoresis", Anal. Chem., 2002. 74: p. 1249-1255.

Hayes, et al., "Demonstration of sandwich and competitive modulated supraparticle fluoroimmunoassay applied to cardiac protein biomarker myoglobin", Analyst, 2009, 134, 533-541.

Hayes, et al., "Effects of Buffer pH on Electroosmotic Flow Control by an Applied Radial Voltage for Capillary Zone Electrophoresis", Anal. Chem., 1993. 65(1): p. 27-31.

Hayes, et al., "Electroosmotic Flow Control and Monitoring with an Applied Radial Voltage for Capillary Zone Electrophoresis", Anal. Chem., 1992. 64(5): p. 512-516.

Hayes, et al., "Electroosmotic Flow Control and Surface Conductance in Capillary Zone Electrophoresis", Anal. Chem., 1993. 65: p. 2010-2013.

Hayes, et al., "Extension of external voltage control of electroosmosis to high-pH buffers", Analytical Chemistry, 1999. 71(17): p. 3793-3798.

Hayes, et al., "Flow-based microimmunoassay", Analytical Chemistry, 2001. 73(24): p. 5896-5902.

Hayes, et al., "Preservation of NADH voltammetry for enzyme-modified electrodes based on dehydrogenase", Analytical Chemistry, 1999. 71(9): p. 1720-1727.

Hayes, et al., "Prospects for the use of Capillary Electrophoresis in Neuroscience", Capillary Electrophoresis Technology, N.A. Guzman, Editor. 1993, Marcel Dekker: NY.

Hellmich, et al., "Poly(oxyethylene) based surface coatings for poly(dimethylsiloxane) microchannels", Langmuir, 2005. 21(16): p. 7551-7557.

Horiuchi, et al., "Electroosmosis with step changes in zeta potential in microchannels", AIChE Journal, 2007. 53(10) p. 2521-2533.

Huang, et al., "Coating of poly(dimethylsiloxane) with n-dodecyl-beta-D-maltoside to minimize nonspecific protein adsorption", Lab on a Chip, 2005. 5(10): p. 1005-1007.

Ikeda, et al., "Measurement of dielectrophoretic mobility of single micro-particles in a flow channel", Analyst, 2005. 130(10): p. 1340-1342.

Jones, et al., "Blood Cell Capture in a sawtooth Dielectrophoretic Microchannel", Anal. Bioanal. Chem. (2011) 401: p. 2103-2111.

Jung, et al., "A cell-repellent sulfonated PEG comb-like polymer for highly resolved cell micropatterns", Journal of Biomaterials Science-Polymer Edition, 2008. 19(2): p. 161-173.

Lee, et al., "An aqueous-based surface modification of poly(dimethylsiloxane) with poly(ethylene glycol) to prevent biofouling", Langmuir, 2005. 21(25): p. 11957-11962.

Liu, et al., "Poly(dimethylsiloxane) microchips with two sharpened stretching tips and its application to protein separation using dynamic coating", Chinese Journal of Chemistry, 2007. 25(2): p. 190-195.

Lucy, et al., "Non-covalent capillary coatings for protein separations in capillary electrophoresis", Journal of Chromatography A, 2008. 1184(1-2): p. 81-105.

MacDonald, et al., "Highly efficient protein separations in capillary electrophoresis using a supported bilayer/diblock copolymer coating", Journal of Chromatography A, 2006. 1130(2): p. 265-271.

Mahanti, et al., "Improved detectability and signal strength for rotating phase fluorescence immunoassays through image processing", The Analyst, Analyst. Jan. 21, 2011;136(2):365-367.

Mahanti, et al., "Particle velocimetry data from COMSOL model of micro-channels", Proceedings of COMSOL User Conference Oct. 7-9, 2010, Boston MA,USA, Nov. 2010.

Mahanti, et al., "Spatio-temporal image analysis of particle streaks in micro-channels for low-cost electro-hydrodynamic flow characterization", 33rd Annual Inter-national Conference of the IEEE EMBS Boston, Massachusetts USA, Aug. 30-Sep. 3, 2011, pp. 4026-4029.

Mansfield, et al., "Preparation and characterization of cross-linked phospholipid bilayer capillary coatings for protein separations", Analytical Chemistry, 2007. 79(8): p. 3135-3141.

Mohamadi, et al., "Dynamic coating using methylcellulose and polysorbate 20 for nondenaturing electrophoresis of proteins on plastic microchips", Electrophoresis, 2007. 28(5): p. 830-836.

Pacheco, et al., "A study on the condition for differential electrophoretic transport at a channel entrance", Electrophoresis, 2007. 28(7): p. 1027-1035.

Phayre, et al., "Effects of pH Gradients on Liposomal Charge States Examined by Capillary Electrophoresis", Langmuir, 2002. 18: p. 6499-6503.

Polson, et al., "Electroosmotic Flow Control of Fluids on a Capillary Electrophoresis Microdevice Using an Applied External Voltage", Anal. Chem., 2000. 72: p. 1088-1092.

Polson, et al., "Electrophoretic focusing preconcentration technique using a continuous buffer system for capillary electrophoresis", Journal of Microcolumn Separations, 2000. 12(2): p. 98-106.

Polson, et al., "Microfluidics—Controlling fluids in small places", Analytical Chemistry, 2001. 73(11): p. 312A-319A.

Pysher, et al., "Effects of Deformability, Uneven Surface Charge Distributions and Multipole Moments on Biocolloid Electrophoretic Migration", Langmuir, 2005. 21: p. 3572-3577.

Pysher, et al., "Electrophoretic and dielectrophoretic field gradient technique for separating bioparticles", Analytical Chemistry, 2007. 79(12): p. 4552-4557.

Pysher, et al., "Examination of the Electrophoretic Behavior of Liposomes", Langmuir, 2004. 20: p. 4369-4375.

Reschke, et al., "A theoretical and experimental study of the electrophoretic extraction of ions from a pressure driven flow in a microfluidic device", Lab on a Chip, 2009. 9(15): p. 2203-2211.

Reschke, et al., "Simultaneous separation and detection of cations and anions on a microfluidic device with suppressed electroosmotic flow and a single injection point", Analyst, 2010. 135(6): p. 1351-1359.

Ribot, et al., "Standardization of pulsed-field gel electrophoresis protocols for the subtyping of *Escherichia coli* O157: H7 *Salmonella*, and Shigella for PulseNet", Foodborne Pathogens and Disease, 2006. 3(1): p. 59-67.

(56) References Cited

OTHER PUBLICATIONS

Roa, et al., "Automated characterization of bacteria in confocal microscope images", Computer Vision and Pattern Recognition Workshops, 2008. CVPRW '08, pp. 1-8 2008.

Ros, et al., "Bioanalysis in structured microfluidic systems", Electrophoresis, 2006. 27(13): p. 2651-2658.

Rosario, et al., "Lotus Effect Amplifies Light-Induced Contact Angle Switching", Journal of Physical Chemistry A, 2004. 108: p. 12640-12642.

St. Claire, et al., "Heat index flow monitoring in capillaries with interferometric backscatter detection", Analytical Chemistry, 2000. 72(19): p. 4726-4730.

Staton, et al., "Characterization of particle capture in a sawtooth patterned insulating electrokinetic microfluidic device", Electrophoresis, 2010. 31: p. 3634-3641.

Staton, et al., "Manipulation and capture of Ab amyloid fibrils and monomers by DC insulator gradient dielectrophoresis (DC-iGDEP)", Analyst, 2012. 137(14): p. 3227-3229.

Sugiura, et al., "Surface modification of polydimethylsiloxane with photo-grafted poly(ethylene glycol) for micropatterned protein adsorption and cell adhesion", Colloids and Surfaces B-Biointerfaces, 2008. 63(2): p. 301-305.

Swaminathan, et al., "PulseNet: The molecular subtyping network for foodborne bacterial disease surveillance, United States", Emerging Infectious Diseases, 2001. 7(3): p. 382-389.

Wang, et al., "Covalent modified hydrophilic polymer brushes onto poly(dimethylsiloxane) microchannel surface for electrophoresis separation of amino acids", Journal of Chromatography A, 2008. 1192(1): p. 173-179.

Watarai, et al., "In situ measurement of dielectrophoretic mobility of single polystyrene microparticles", Langmuir, 1997.13(8): p. 2417-2420.

Weiss, et al., "Capillary isoelectric focusing coupled offline to matrix assisted laser desorption/ionization mass spectrometry", Journal of Chromatography A, 2010. 1217(1): p. 179-182.

Weiss, et al., "Dielectrophoretic Mobility Determination in DC Insulator-Based Dielectrophoresis", Electrophoresis, 2011, 32, 2292-2297.

Windman, et al., "Microfluidics for ultrasmall-volume biological analysis", Advances in Chromatography, vol. 42. 2003. p. 241-267.

Wong, et al., "Surface molecular property modifications for poly(dimethylsiloxane) (PDMS) based microfluidic devices", Microfluidics and Nanofluidics, 2009. 7(3): p. 291-306.

Zhang, et al., "Poly(N,N-dimethylacrylamide)-grafted polyacrylamide: A self-coating copolymer for sieving separation of native proteins by CE", Electrophoresis, 2006. 27(15): p. 3086-3092.

Zhou, et al., "Convenient Method for Modifying Poly(dimethylsiloxane) with Poly(ethylene glycol) in Microfluidics", Analytical Chemistry, 2009. 81(16): p. 6627-6632.

* cited by examiner

BACTERIAL IDENTIFICATION

PRIORITY OF INVENTION

This application is a divisional of U.S. patent application Ser. No. 13/797,181 filed Mar. 12, 2013, and claims priority to U.S. Provisional Application No. 61/638,316, filed Apr. 25, 2012. The entire content of the applications referenced above are hereby incorporated by reference herein by reference.

BACKGROUND OF THE INVENTION

Among the large number of illnesses caused by bacteria, perhaps the most common is diarrhea. According to the World Health Organization, of the millions of deaths each year worldwide from diarrheal disease, most are caused by contaminated food and water, poor hygiene, or improper sanitation practices. Pathogenic *Escherichia coli* (*E. coli*) accounts for the second largest cause of these infections. Even in the United States, where mechanisms and practices are well developed to prevent transmission; there were over thirty thousand hospitalizations and nine hundred deaths involving *E. coli* between 1982 and 2002. Beyond diarrhea, the common and preeminent virulent O157:H7 serotype can cause severe or even fatal damage to vascular, urinary and nephrology systems. While this provides a specific and poignant example, there are a myriad of other clinically significant pathogenic bacteria along with innumerable benign and beneficial ones. It is of utmost importance to quickly detect and accurately differentiate between serotypes to effect appropriate treatment of patients and minimize spread of dangerous strains.

In response to recent non-O157 outbreaks of toxigenic *E. coli*, in January 2011 the US congress passed the Food Safety Modernization Act, which mandates zero tolerance for a number of pathogenic bacteria, including *E. coli* serotypes O157, O26, O45, O103, O111, O121 and O145. Producers have been required to hold products for a week or more until cleared; this requirement has had a significant impact on the cost of food production. The CDC has identified improved surveillance of *E. coli* and development of tools for more rapid detection of emerging diarrheagenic *E. coli* strains as both challenges and opportunities. Yet these pathogenic strains must be detected within a microbial ecosystem containing huge numbers of Enterobacteriaceae.

There are standard laboratory methods for the detection, isolation and identification of pathogenic *E. coli*, where human capital is the constraining resource. Correct identification of pathogen-positive samples using serotyping requires extensive training. Conventional microbiological methods require approximately two days to perform primary enrichment, selective enrichment, and plating on different media for isolation of bacterial species and serotypes present in a sample. Additional characterization linking pathogen to contamination source requires serological bio-typing of cellular and flagellar antigens, requiring another 2-3 days. The addition of genotyping provides toxigenicity information based on plasmid toxin genes and requires approximately 3 days; this can be simultaneous with serology but requires resourcing of additional laboratory personnel. Genotyping by pulsed-field gel electrophoresis allows more refined comparison of strains on a global scale, but requires subjective individual judgment of banding patterns by an even more extensively trained certified analyst. In clinical situations, as this labor intensive and time consuming process is performed, the patient is being treated symptomatically or for a non-specific infection and the pathogenic strain continues to spread to other victims. For producers, any decrease in the time to determine *E. coli* O-side antigen would allow removal of contaminated food product from commerce more quickly, improving morbidity and mortality outcomes of humans and animals.

SUMMARY OF THE INVENTION

In one embodiment, the invention provides a DC-iGDEP device for separating bacterial serotypes comprising one or more members defining one or more separation chambers, each separation chamber defining a microfluidic channel having a top, bottom and two sides, the channel having a channel inlet port at a proximal end of the channel and a channel outlet port at a distal end of the channel, and further having an electrode disposed at the proximal end of the channel, an electrode disposed at the distal end of the channel, one or more sets of teeth, each set having two teeth disposed opposite from one another at the sides of and extending into the microfluidic channel end and defining a gate in the channel, wherein the gates defined by the one or more sets of teeth are 1 to 500 microns across, each tooth having a base at the distal end of the tooth disposed at a side of the microfluidic channel and a tip disposed at the proximal end of the tooth, and one or more access ports defined by one or more members, each access port allowing fluid communication through the one or members to the channel in a separation chamber between the channel inlet port and the channel outlet port.

The one or more access ports may allow fluid communication to the channel at a gate, to the channel proximal to a gate, or to the channel distal to a gate.

In one embodiment, the one or more members may define a sample reservoir in fluid communication with the channel of a separation chamber downstream from the channel inlet port for the channel for introduction of a sample into the channel.

In one embodiment, the width of the gates in a channel decreases in the direction from the channel inlet port to the channel outlet port. In one embodiment, the width of each gate in a channel decreases in the direction of the channel inlet port to the channel outlet port.

In one embodiment, one or more sets teeth have a triangular shape, an asymmetric shape, or a crescent shape. In one embodiment, one or more teeth have a starred, fractal or rounded shape at the tip of the one or more teeth.

In one embodiment, the device further includes a sensor, the sensor having an image capture system capable of capturing one or more images in the channel. The one or more images may be still images or live images.

In one embodiment, the sensor is capable of detecting the presence of bacterial cells in the channel.

In one embodiment, the sensor can detect the presence of bacterial cells at one or more locations in the channel.

In one embodiment, the sensor can detect the presence of bacterial cells at one gate location in the channel.

In one embodiment, the sensor comprises a microscope. The microscope may be a miniaturized digital microscope capable of obtaining images at one or more locations in a channel. The miniaturized digital microscope may be capable of imaging one or more channels. The miniaturized digital microscope may be capable of capturing images in the one or more separation chambers using conventional microscopy optics.

In one embodiment, the sensor comprises one or more optical elements.

In one embodiment, the sensor further comprises an image analysis system to analyze one or more images from the image capture system. In one embodiment, the image analysis system comprises computer readable media comprising image analysis software and further comprises comprising a processor for executing the software, wherein the execution of the software allows the image analysis system to perform one or more tasks selected from the group consisting of: detecting the presence of bacteria in an image, identifying bacteria species in an image, identifying bacteria serotypes in an image, detecting motility of bacteria in an image, and determining the number of bacteria in an image.

In one embodiment, the image analysis system is capable of detecting the presence of bacteria in an image.

In one embodiment, the image analysis system is capable of detecting movement of bacteria in an image.

In one embodiment, the image analysis system is capable of detecting the number of bacteria in an image.

In one embodiment, the device comprises two or more separation chambers wherein the one or more members further define a device channel inlet port and wherein the device channel inlet port is capable of fluid communication with the channel inlet port of each of the two or more separation chambers.

In one embodiment, the invention provides a method of separating bacterial species and bacterial serotypes present in a sample comprising (a) providing a DC-iGDEP device, the device comprising one or more members defining one or more separation chambers, each separation chamber defining a microfluidic channel having a top, bottom and two sides, the channel having a channel inlet port at a proximal end and a channel outlet port at a distal end, and further comprising an electrode disposed at the proximal end of the channel, an electrode disposed at the distal end of the channel, and one or more sets of teeth, each set comprising two teeth disposed opposite from one another at the sides of and extending into the microfluidic channel and defining a gate in the channel, wherein the gates defined by the one or more sets of teeth are 1 to 500 microns across, each tooth having a base disposed at a side of the microfluidic channel and a tip disposed at a gate, (b) loading a loading volume of the sample into the channel inlet port, applying an electrical field across the electrodes in the one or more separation chambers to separate the bacterial species or bacterial serotypes in the sample, and identifying the bacterial species or bacterial serotypes present within the sample based on their behavior in the field present in the one or more channels.

In one embodiment, the bacterial serotypes are *E. coli* serotypes.

In one embodiment, one or more of the bacterial serotypes are pathogenic *E. coli* serotypes.

In one embodiment, the bacterial serotypes are *E. coli* serotypes selected from the group consisting of O157, O157:H7, O6:H6, O26, O45, O103, O111, O121 and O145.

In one embodiment, the bacteria are *Salmonella enteretica* serovars selected from the group consisting of *Salmonella enteritidis, Salmonella paratyphi* A, *Salmonella paratyphi* B, *Salmonella paratyphi* C and *Salmonella typhi*.

In one embodiment, the bacteria are of genus *Clostridium*, selected from the group consisting of *Clostridium botulinum, Clostridium difficile, Clostridium perfringens, Clostridium septicum, Clostridium sordellii,* and *Clostridium tetani*.

In one embodiment, the sample is a biological sample.

In one embodiment, the biological sample is blood, serum, saliva, spinal fluid, urine, or fecal material.

In one embodiment, the sample is a food sample.

In one embodiment, the sample is derived from a food sample.

In one embodiment, the device further comprises one or more access ports defined by the one or more members, each access port allowing fluid communication through the one or members to the channel between the channel inlet port and the channel outlet port wherein a bacterial species or bacterial serotype localizes at or near the access port when a field is applied across the electrodes in the one or more separation chambers, and the method further comprises removing an aliquot of the bacterial species or bacterial serotype localized at or near the access port.

DETAILED DESCRIPTION OF THE INVENTION

Dielectrophoresis (DEP) exploits the force exerted by a non-uniform electric field on a population of polarizable particles to separate various subsets of the particles in the population. In general terms, DEP occurs as a result of the force exerted by the external field on the field-induced dipole moment of the polarized particle. However, the electrodes are traditionally embedded within the separation chamber, which can cause undesirable electrochemical reactions and gas generation at the surfaces of the electrodes. Although the use of AC rather than DC voltage helps to minimize these effects, it does not eliminate them. Traditional DEP devices are also generally limited to separating two distinctly different components, one that collects in the high field strength regions (typically located on, or near, the electrodes) and one that does not.

Insulator gradient dielectrophoresis (DC-iGDEP) differs from traditional DEP in that a DC voltage is applied to electrodes located in remote inlet and outlet reservoirs, and the field non-uniformities are generated by the geometric configuration of insulators located within the channel. The theoretical basis of the technique and proof-of-principle has been demonstrated using latex spheres. In subsequent studies, the technique was used to concentrate and isolate live and dead bacteria except that DC-iGDEP allows the longitudinal separation of mixtures as opposed to a simply bifurcation of two components. Geometric shapes were exploited for bacteria separation from latex particles.

Figure 1:
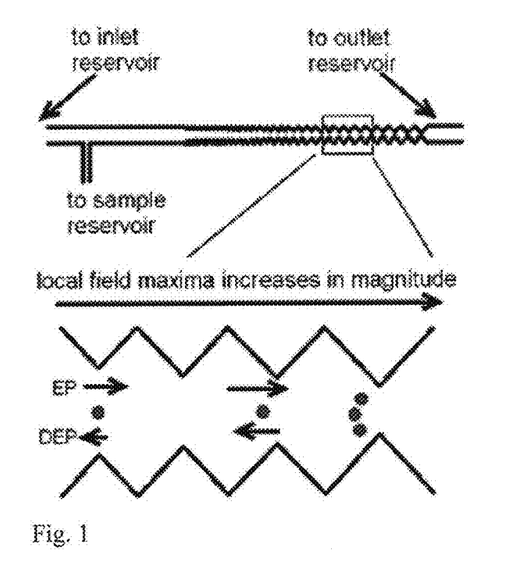
FIG. 1 shows a schematic of a representative device and graphical depiction of the separation and trapping mechanism.

A schematic of a representative device and graphical depiction of the separation and trapping mechanism are shown in FIG. 1. For these studies, the series of field gradient regions was created by designing the channel walls in a 'saw-tooth' pattern. Each pair of opposing teeth establishes a local gradient region that acts as separate dielectrophoretic trap; the local field maxima are located at the tips of the teeth and the minima at their base. The physical parameters of the teeth (including width, height, angle, and proportions) determine the strength of each trap (defined by the local gradient and magnitude of the field within it). Therefore, gradient regions, or dielectrophoretic traps, of differing strengths can be created by varying the physical parameters of the teeth throughout the device. Here, the devices were designed so that a series of dielectrophoretic traps of gradually increasing strength is established along the length of the channel; the strength of the traps is relatively small near the inlet and increases incrementally in the direction of the outlet.

DC-iGDEP offers several advantages compared to traditional DEP. The use of remote electrodes avoids many of the problems associated with embedded electrodes, such as electrochemical reactions and gas generation at the electrode surfaces. Additionally, the electrophoretic field can be generated by applying DC rather than AC voltage. Use of a DC field can be advantageous because it can be used to drive both electrophoretic and dielectrophoretic transport, allowing greater control over particle movement. The technique produces sequential, spatially resolved separations by simultaneously exploiting electrophoretic, electroosmotic, and dielectrophoretic transport mechanisms. Electrophoresis and electroosmosis may be used to transport the particles through a channel containing a series of progressively stronger field gradient regions. As the particles are transported through the channel, they are isolated according to their characteristic physical properties in response to electrophoretic and dielectrophoretic forces. Because this technique relies on both electrophoretic and dielectrophoretic forces, it accesses a much richer set of properties to accomplish separation than many other techniques. Furthermore, the incorporation of electrophoretic transport mechanisms allows for greater control over sample introduction and particle movement, and for faster separations.

The DC-iGDEP apparatus may be tuned or adjusted as disclosed above in order ensure that bacterial species such as *Lactobacillus* spp., *Bifidobacterium* spp., Non-pathogenic *E. coli, Streptobacillus* spp, including *Streptobacillus salivarius, Saccharomyces* spp. Including *Saccharomyces boulardii* and *Clostridium* spp, including *Clostridium butyricum*) occupies a unique location away from the target bacterial species or serotype, such as *E. coli* O157:H7.

Different strains, and even different metabolic states, of *E. coli* may differ in physical size, shape and structure, e.g. in terms size and/or number of flagella, fimbriae, fibrils and pili. The identifying antigens of *E. coli* serotypes differ in charge and hydrophobicity, which are related to local dipole moment of a peptide; based on data from the Immune Epitope Database, the O157:H7 antigen has a calculated charge of +25 while O55:H7 antigen has +18. Thus different serotypes or strains would have sufficiently different charge, polarizability and coefficient of friction, hence different electrophoretic and dielectrophoretic susceptibilities, that would allow for convenient separation as disclosed herein.

Device Fabrication. Microfluidic devices for DC-iGDEP may be fabricated using standard photolithography, fabrication, and bonding techniques. Devices may be fabricated from Schott D263 glass wafers (S. I. Howard Glass Company, Worcester, Mass.) and polydimethylsiloxane (PDMS). The photomasks may be designed using AutoCAD (Autodesk, Inc., San Rafael, Calif.) and printed as photoplots. Devices may be fabricated both completely from glass and from PDMS with a glass cover plate.

The PDMS portion of the device may be fabricated using channel molds fabricated from resists using standard photolithography techniques. Channel inlet and channel outlet ports holes may be made using a hole punch or other suitable tool, and then the PDMS channel may be sealed to a glass cover plate by plasma oxidation, followed by contact sealing.

In one embodiment, PDMS (Sylgard 184, Dow/Corning, Midland, Mich.) may be poured over a photoresist template patterned on a silicon wafer and allowed to cure. The PDMS portion may be oxidized via oxygen-plasma treatment and then irreversibly bonded to a glass slide.

Two to three millimeter diameter holes may be punched through the PDMS at each end of the channel to form the channel inlet and channel outlet ports and to access reservoirs on either end of the channel defined by the template. Electrodes (such as platinum electrodes) may be inserted through the channel inlet and channel outlet ports at each end of the microchannel and used to apply potential across the microchannel.

These designs should produce acceptable results; however, PDMS/glass devices may be preferable for several reasons: (1) The profile of etched glass channels can be distorted due to anisotropic etching; although the channel wall profile appears to be maintained when fabricated from PDMS; (2) Bacterial adhesion and fouling of the PDMS/glass devices appears to occur less often; (3) The fabrication process of PDMS/glass devices is easier, less costly, and takes considerably less time.

Adsorption of materials to the surfaces of the microfluidic device that are in contact with samples can irreversibly remove analytes and induce electroosmosis. Siloxanes (such as polydimethylsiloxane) may be covalently adhered to such surfaces to permanently alter the surface and prevent or minimize adsorbtion to the surface. Such siloxane coated surfaces may be modified using polyethylene glycol (PEG) or POE-based chemistry.

Channel design. Channel depths may be 10-20 μm, and may be up to about 500 μm. Tooth structure is also important in achieving optimal separation. The sets of teeth in each channel generally include pairs of teeth disposed directly opposite from one another in the channel with the distal base of each tooth disposed along the corresponding side of the channel and the proximal tip of each tooth extending into the channel. Generally, the teeth are wider at the base than at the tip. Each of the teeth in the set is generally the same height (measured from base to tip) as the other tooth. Each set of teeth therefore defines a gate within the channel and the width of each gate is measured as the distance between the tips of the teeth in the corresponding set.

Often the width of the gates will decrease in a channel with the gates at the proximal end of the channel being wider than the gates at the distal end of the channel. The width of the gates may decrease with each set of teeth, or decrease every second, third fourth, fifth, sixth or more sets of teeth progressing from the proximal to the distal end of the channel. A modified linear gradient in decreasing width of gates, or other shape that that enhances or optimizes separation may be used. Such shapes may include geometric decreases, logarithmic, exponential, or non-linear systems combining several underlying patterns. Shapes such as crescent shapes and asymmetric systems, may be used in electrode design. These shapes may be used to enhance and optimize isolation and concentration of specific target bacteria. In addition, the rate at which the taper of the electrodes change is an adjustable parameter. Finally, additional shaped insulating structures may be placed at the tips of the teeth to further refine the shape of the field gradient within the gap. Such additional structures may include simple half stars, needle points and fractal patterns.

In one embodiment, the initial tooth height (base to tip) of the channel may be 150 µm, and the width (across the base at the distal end) is the same as the height, 150 µm. The heights and widths of the teeth increase in 10 µm increments after every third tooth in the series. The final tooth height (for the last three sets of teeth) is 240 µm and the width is also 240 µm. In another embodiment, the initial tooth height (base to tip) may be 100 µm and the width (across the base at the distal end) is twice the height, or 200 µm. The height of the teeth increases in 5 µm increments after every third tooth in the series (and widths increase in 10 µm increments). The final tooth height (last three teeth) is 240 µM and the width is 480 µm. In another embodiment, the initial tooth height (base to tip) is 100 µm and the width (across base) is twice the height, or 200 µm. The height of the teeth increases in 5 µm increments (and widths in 10 µm increments) after each tooth in the series. The final tooth height (last tooth) is 240 µm and the width is 480 µm.

Figure 2:
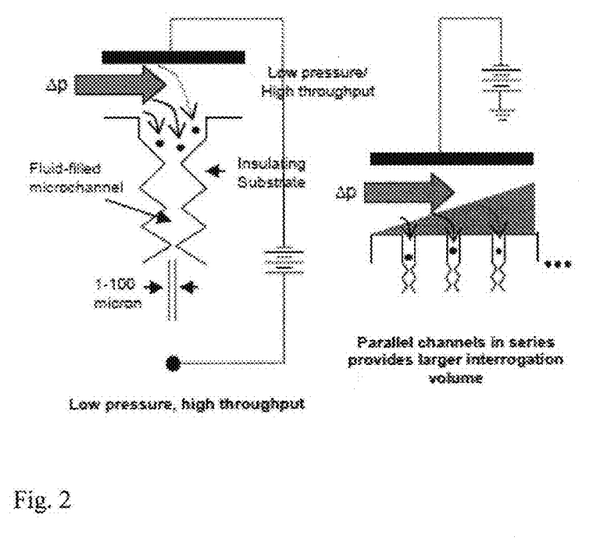
FIG. 2 shows a schematic of a DC-iGDEP device having one separation chamber and a DC-iGDEP device having one separation chamber having more than one separation chamber.

A 'by-pass' flow may be used to increase throughput, thereby accommodating larger sample sizes (See FIG. 2). A single channel is shown on the left side of FIG. 2 with the sample applied at the channel inlet port. Three sets of teeth are shown in this portion of FIG. 2 and the gates are shown to be from 1 to 100 microns across. On the right side of FIG. 2, a device having three separation chambers is shown with a device access port in communication with the channel inlet ports for each of the three separation chambers. This method exposes a stream of fluid flowing past the entrance of a series of parallel DC-iGDEP separation channels. The flowing stream may be under the influence of a lateral electric field, such that appropriately charged species (such as negatively charged bioparticles) may be transported into the channel, without increasing backpressure on the flow stream. The volume flow of the by-pass may be set at 0.1 mL/min so that an entire 1 mL sample can be processed in ten minutes (designs that can accommodate larger flow may be used to achieve faster read times). A dimension of three millimeters (×20 micron height) may be used, accounting for lateral transport rates calculated from bacteria separations in CE and a maximum theoretical efficiency of approximately 87%. Each of the DC-iGDEP channels can have a separate detection element, or the entire device can be imaged or scanned. Also, through parallel and serial processing, the collected samples can be transported to a single location. The depth of the channel may be increased, and this increase will directly offset this dimension without compromising the DEP gradient effects. A doubling of depth will halve the entrance width (a 40 µm depth: 1.5 cm; 80 µm: 7.5 mm, etc.) and proportionally reduce the number of DEP elements in parallel.

Visualization and Data Collection. Separations can be monitored, recorded and analyzed using various sensors. For example, separations may be monitored using a microscope. The microscope can be an inverted microscope, such as an Olympus IX70 equipped with a QICAM ccd camera (Q Imaging Inc.). Smaller devices for imaging bacterial species and serotypes within an apparatus may be utilized. Such smaller devices may provide for visual imaging or may provide for signal detection at one or more locations within a separation chamber where one or more bacterial species and serotypes would be expected to localize. A light source such as a mercury short arc H30 103 w/2 light source (OSRAM) may be used. Other light sources such as halogen lamp or laser source may be used to illuminate a separation chamber or specific locations within the chamber. Images of the separation chamber or specific locations within the chamber may be captured using an image capture system. For example, images may be captured as .tif sequences using a data capture program such as Stream Pix III (version 3.6.0, Norpix). Images may also be captured in other formats (such as .avi) and single still frames retrieved using a program such as Microsoft Windows Movie Maker. Live images within the chamber may also be captured. The still and live images may be analyzed using an image analysis system. The image analysis system will generally have computer readable media with software stored on it. The computer readable media may be accessed using a processor on which the software will run and execute instructions for analysis of the image. The software may provide instructions to allow the image analysis system to detect the presence of bacteria in an image, identify bacteria species in an image, identify bacteria serotypes in an image, detect motility of bacteria in an image, and determine the number of bacteria in an image.

Samples. Samples to be tested may be biological sample such as blood, serum, saliva, spinal fluid, urine, or fecal material. With the exception of most fecal material, the samples may be applied directly to the device. Biological samples may also be solubilized or diluted in a buffer. The sample so obtained should support an electrical flow through the sample.

The sample may also be a food sample. Food samples may include liquids such as milk or fruit or vegetable juices or solid foods such as fruits that have been liquefied. Such liquid or liquefied samples may be diluted in a buffer and applied to the device. The sample may also be derived from a food sample by swabbing the surface of the food sample and introducing any bacteria obtained from the swab into a liquid. The sample may also be derived by rinsing the food sample and saving the rinse liquid. In some cases, the derived samples may be applied directly to the device. In some cases, the derived samples may be cultured to allow for proliferation of bacteria in the derived samples.

Samples applied to the device may be stained with various fluorescent stains (such as VYBRANT™ DiO); however such staining may not be necessary for monitoring separations as disclosed herein.

EXAMPLES

Example 1

*Escherichia coli* Preparation Protocol

Growth Medium: A 1.1 g tablet of dehydrated LB medium (Sigma Aldrich) was added to 50 mL of 18 MΩ deionized water. The solution was gently heated with stirring until all solids dissolved. The solution was then covered and autoclaved.

Bacterial Growth: 5 mL autoclaved LB was added to each of three sterile 10 dram vials. Strains of *E. coli*, frozen on small (approximately 2-mm diameter) beads, were obtained from the State of Arizona Public Health Laboratory. One bead from each strain was used to inoculate three of the four vials. The last vial of growth medium was retained as a control, to ensure that no contamination occurred. Following inoculation of the media with beads, the vials were incubated overnight at 37° C. in a shaker/incubator.

Fluorescent labeling: Following incubation, optical density measurements were taken at 600 nm to ensure sufficient bacterial growth. 1-mL samples of each solution were transferred to microcentrifuge tubes. Bacterial cells contained in these samples were washed 3 times by centrifuging at 2000 rpm for 5 minutes followed by resuspension of the cell pellet in 2 mM phosphate buffer (pH 7.4). A 5 µL aliquot of Vybrant DiO Cell-labeling Solution (Invitrogen) was added to the resuspended cells then gently vortexed. The samples were incubated in a 37° C. water bath for 20 minutes. Following incubation, cells were again washed 3 times by centrifugation and resuspension in phosphate buffer. At this point, cells are ready for introduction into microfluidic channels.

Example 2

Separation of *E. coli* Serotypes

*E. coli* bacterial strains in buffer may be separated using DC-iGDEP apparatus. In particular, three closely related *E. coli* serotypes (ATCC 25922 (O6:H1); O55:H7; O157:H7) have been separated from each other using DC-iGDEP apparatus. *E. coli* samples were dispersed in phosphate buffer and introduced into the channel using hydrostatic pressure. The dielectromicrofluidic design is a microfluidic channel cast in dielectric insulator approximately 3 cm long by a variable width starting with 350µ at inlet, and with wall cast in an opposing sawtooth configuration with opposing sawteeth separated by varying distances ranging from 300µ to 30µ at the outlet. The channel was imaged using an Olympus IX70 inverted microscope, and the 4 cm length of the channel was scanned manually by manipulating the caliper dial of the slide stage, while the voltage on the channel was tuned. *E. coli* serotype ATCC 25922 (O6:H1) was trapped and concentrated at the 30µ gates beginning at 500V, at the 90µ gates beginning at 1200V and at the 300µ gate at 1750V. The O55:H7 serotype capture onset at the 30µ gate at occurred 1200V. The O157:H7 was captured at the 30µ gate beginning when 1500V was applied, and at the 90µ gates at 2000V. This data shows that the voltage required to trap these three serotypes varies by factor of three and provides a demonstration that bacterial strains can be differentially sequestered in this system. O157:H7 and O55:H7 have the same flagellar antigen suggesting that separation based on somatic antigens only is possible.

Example 3

Images of *E. coli* O157:117 Capture in DC-iGDEP Apparatus

Figure 3:
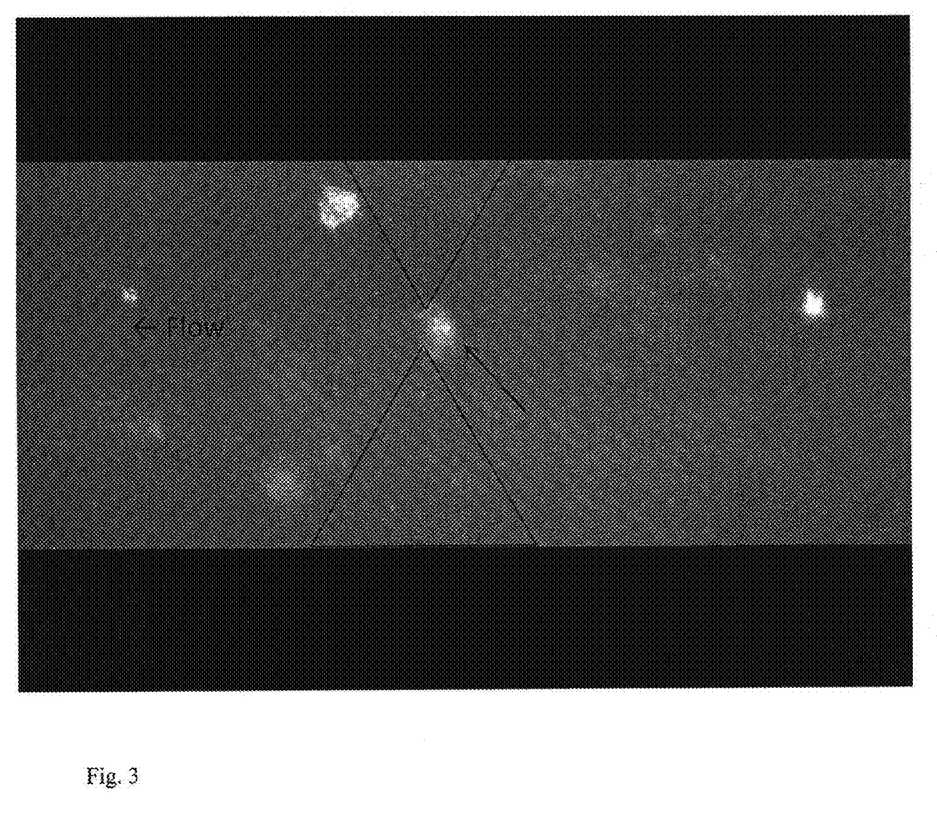
FIG. 3 shows a portion of a channel in a DC-iGDEP device where bacterial cells have begun to accumulate at a gate shortly after a potential has been applied across the channel.
Figure 4:
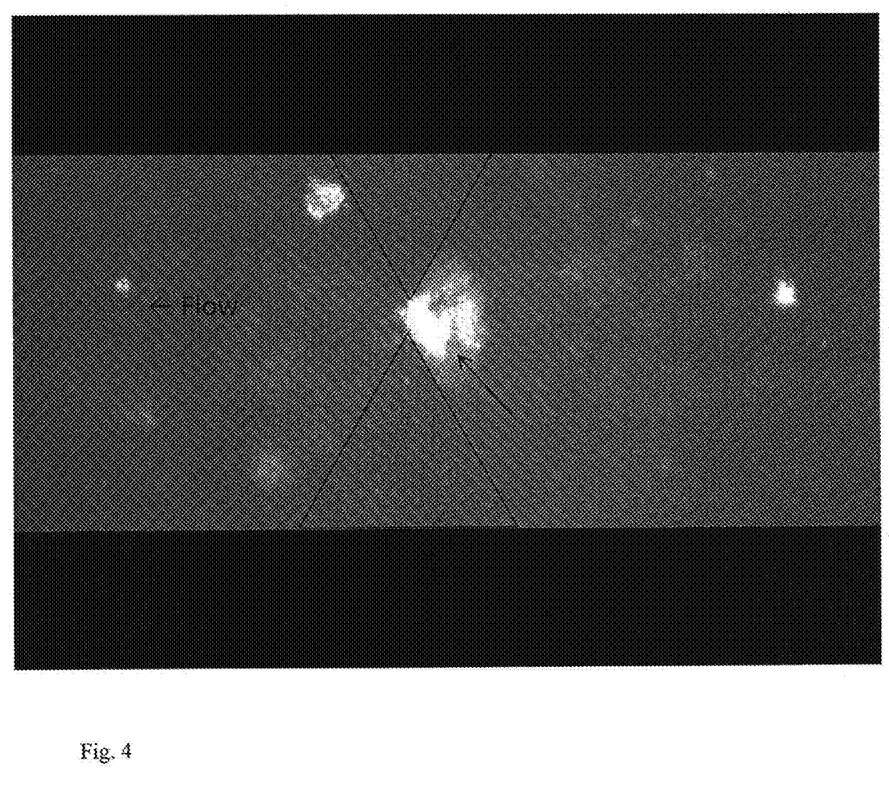
FIG. 4 shows the same portion of a channel in a DC-iGDEP device where bacterial cells have continued to accumulate at the gate while the potential continues to be applied across the channel.
Figure 5:
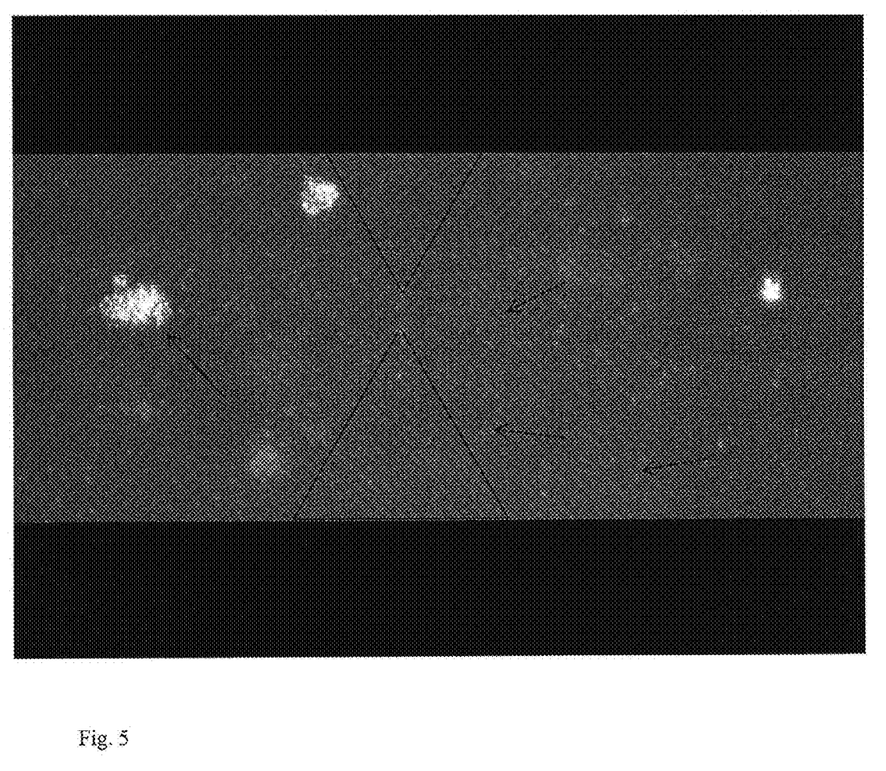
FIG. 5 shows the same portion of a channel in a DC-iGDEP device where much of the accumulated bacterial cells have passed through the gate after the potential was removed.

DC-iGDEP Apparatus using PDMS bonded to glass plates were prepared as described above. *E. coli* O157:H7 was introduced into the channel and electrodes were introduced. A potential of 600 volts was then applied across the chamber. FIGS. 3 through 5 show a bright field image of a portion of the chamber at 100× magnification. In each Figure, an approximate drawing of a 30 µm PDMS gate is shown as opposing isosceles triangles. Flow of the bacterial cells due to the electrical forces on the cells is from right to left in this figure. Accumulation of *E. coli* O157:H7 cells at a 30 µm gate in the apparatus shortly after application of the voltage is shown in FIG. 3 (solid arrow). FIG. 4 shows increasing accumulation of *E. coli* O157:H7 cells at the 30 µm gate (solid arrow). FIG. 5 shows the chamber shortly after the voltage has been cut off. *E. coli* O157:H7 cells that had been accumulating on the right side of the gate have passed through to the left side of the gate (solid arrow). Individual cells are indicated in FIG. 5 on the right side of the gate (dashed arrows). These cells appeared to be motile even after the application of the voltage in the chamber.

Although the foregoing specification fully discloses and enables the present invention, it is not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:
1. A method of separating bacterial species and bacterial serotypes present in a sample comprising,
 (a) providing a direct current insulator gradient dielectrophoresis (DC-iGDEP) device, the device comprising one or more members defining one or more separation chambers,
  each separation chamber defining a microfluidic channel having a top, bottom and two sides, the channel having a channel inlet port at a proximal end and a channel outlet port at a distal end, and further comprising an electrode disposed at the proximal end of the channel, an electrode disposed at the distal end of the channel, one or more sets of teeth, each set comprising two teeth disposed opposite from one another at the sides of and extending into the microfluidic channel and defining a gate in the channel, wherein the gates defined by the one or more sets of teeth are 1 to 500 microns across and establish local gradient regions that act as separate dielectrophoretic traps, each tooth having a base disposed at a side of the microfluidic channel and a tip disposed at a gate, (b) loading a loading volume of the sample into the channel inlet port, (c) applying an electrical field across the electrodes in the one or more separation chambers to separate the bacterial species or bacterial serotypes in the sample, and (d) identifying the bacterial species or bacterial serotypes present within the sample based on their behavior in the field present in the one or more channels.

2. The method of claim 1, wherein the bacterial serotypes are *E. coli* serotypes.

3. The method of claim 1, wherein the bacterial serotypes are *E. coli* serotypes selected from the group consisting of O157, O157:H7, O6:H6, O26, O45, O103, O111, O121 and O145.

4. The method of claim 1, where the bacteria are *Salmonella enteretica* serovars selected from the group consisting of *Salmonella enteritidis, Salmonella paratyphi* A, *Salmonella paratyphi* B, *Salmonella paratyphi* C and *Salmonella typhi*.

5. The method of claim 1, where the bacteria are of genus *Clostridium*, selected from the group consisting of *Clostridium botulinum, Clostridium difficile, Clostridium perfringens, Clostridium septicum, Clostridium sordellii,* and *Clostridium tetani*.

6. The method of claim 1, wherein the sample is a biological sample.

7. The method of claim 1, wherein the sample is a food sample, or is derived from a food sample.

8. The method of claim 1, wherein the device further comprises one or more access ports defined by the one or more members, each access port allowing fluid communication through the one or more members to the channel between the channel inlet port and the channel outlet port wherein a bacterial species or bacterial serotype localizes at or near the access port when a field is applied across the electrodes in the one or more separation chambers, the method further comprising removing an aliquot of the bacterial species or bacterial serotype localized at or near the access port.

* * * * *